US009464303B2

(12) United States Patent
Burke (10) Patent No.: US 9,464,303 B2
(45) Date of Patent: *Oct. 11, 2016

(54) APPLICATIONS OF THE ROTATING PHOTOBIOREACTOR

(71) Applicant: Dennis A. Burke, Olympia, WA (US)

(72) Inventor: Dennis A. Burke, Olympia, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/544,078

(22) Filed: Nov. 20, 2014

(65) Prior Publication Data

US 2015/0079651 A1 Mar. 19, 2015

Related U.S. Application Data

(60) Division of application No. 13/987,795, filed on Sep. 3, 2013, now Pat. No. 8,895,279, which is a continuation-in-part of application No. 13/373,860, filed on Dec. 1, 2011, now Pat. No. 8,637,304.

(60) Provisional application No. 61/460,219, filed on Dec. 29, 2010, provisional application No. 61/743,380, filed on Sep. 4, 2012.

(51) Int. Cl.

| | |
|---|---|
| *C12P 7/16* | (2006.01) |
| *C12N 13/00* | (2006.01) |
| *C12P 3/00* | (2006.01) |
| *C12P 7/04* | (2006.01) |
| *C12M 1/00* | (2006.01) |
| *C12M 1/107* | (2006.01) |
| *C12N 1/12* | (2006.01) |
| *C12P 1/00* | (2006.01) |
| *C12P 5/00* | (2006.01) |
| *B01D 53/26* | (2006.01) |
| *C07C 29/74* | (2006.01) |
| *B01D 53/84* | (2006.01) |

(52) U.S. Cl.
CPC ............. *C12P 7/16* (2013.01); *B01D 53/268* (2013.01); *C07C 29/74* (2013.01); *C12M 21/02* (2013.01); *C12M 21/04* (2013.01); *C12M 23/58* (2013.01); *C12M 47/18* (2013.01); *C12N 1/12* (2013.01); *C12N 13/00* (2013.01); *C12P 1/00* (2013.01); *C12P 3/00* (2013.01); *C12P 5/00* (2013.01); *C12P 7/04* (2013.01); *B01D 53/84* (2013.01); *B01D 2257/504* (2013.01); *C12P 2201/00* (2013.01); *Y02E 50/10* (2013.01); *Y02E 50/343* (2013.01); *Y02P 20/152* (2015.11); *Y02P 20/59* (2015.11)

(58) Field of Classification Search
None
See application file for complete search history.

(56) References Cited

U.S. PATENT DOCUMENTS

| | | | |
|---|---|---|---|
| 3,598,726 | A * | 8/1971 | Welch ........................ 210/602 |
| 4,324,068 | A | 4/1982 | Anthony |
| 6,110,370 | A | 8/2000 | Van Hille et al. |
| 7,416,644 | B2 | 8/2008 | Bonde |
| 7,806,957 | B1 | 10/2010 | Burke |
| 8,241,895 | B2 | 8/2012 | Hu et al. |
| 8,361,786 | B2 | 1/2013 | Hu et al. |
| 8,367,378 | B2 | 2/2013 | Balan et al. |
| 8,394,611 | B2 | 3/2013 | Dale et al. |
| 8,409,852 | B2 | 4/2013 | Redford |
| 8,426,173 | B2 | 4/2013 | Bramucci et al. |
| 8,445,236 | B2 | 5/2013 | Hennessey et al. |
| 8,460,906 | B2 | 6/2013 | Contag et al. |
| 8,497,105 | B2 | 7/2013 | Walther et al. |
| 2007/0102352 | A1 | 5/2007 | Burke |
| 2008/0302722 | A1 | 12/2008 | Burke |
| 2011/0104790 | A1 | 5/2011 | Kassebaum et al. |
| 2011/0151507 | A1 | 6/2011 | va Walsem et al. |

FOREIGN PATENT DOCUMENTS

| | | | |
|---|---|---|---|
| FR | WO 2011/003962 | * | 1/2011 |
| WO | WO 2009/032143 | * | 3/2009 |

OTHER PUBLICATIONS

Yamaguchi et al. "Biodegradation of hydrocarbons by Prototheca zopfii in rotating biological contactors" Process Biochemistry 35 (1999) 403-409.*
Przytocka-Jusiak et al. "Removal of Nitrogen From Industrial Wastewaters With the Use of Algal Rotating Disks and Denitrification Packed Bed Reactor" Water Res. vol. 18. No. 9. pp. 1077-1082. 1984.*
Zimmo et al. "Comparison of ammonia volatilisation rates in algae and duckweed-based waste stabilisation ponds treating domestic wastewater" Water Research 37 (2003) 4587-4594.*
Park et al. "Ammonia removal from anaerobic digestion effluent of livestock waste using green alga *Scenedesmus* sp." Bioresource Technology 101 (2010) 8649-8657.*
Casey, T.J. Unit treatment processes in water and wastewater engineering. Chechester; New Yorl: Wiley.
Corbitt, R.A. (1990). Standard Handbook of Environmental Engineering. New York: McGraw-Hill.
Design of Municipal Wastewater Treatment Plants. (1992). Alexandria, VA: Water Environment Federation; N.Y., N.Y.: American Society of Civil Engineers. Droste. R.L. (1997).
Demirbas, A., & Demirbas, M.F. (2010). Algae as a new source of biodiesel. Springer.
Eddy, M. & Tchobanoglous, G., Burton, F.L. & Stensel, H.D. Theory and Practice of Wastewater Treatment. New York: J. Wiley (2003).
Ezeji, T.C., Karcher, P.M., Qureshi, N. & Blaschek, H.P. (2005). Improving Performance of a Gas Stripping-based recov-ery system to remove butanol. Bioprocess Biosys Eng 27(3):207.

(Continued)

*Primary Examiner* — Thane Underdahl (74) *Attorney, Agent, or Firm* — Brian J. Coyne (57) ABSTRACT

A method to recover and harvest nutrients and volatile gases such as alcohols from a liquid stream using a fixed film bioreactor. The method includes a means of concentrating product gas stripped from a bioreactor.

18 Claims, 6 Drawing Sheets

(56) References Cited

OTHER PUBLICATIONS

Fulks, G., FiSher, G.B., Rahmoeller, K., Wu, M.C., D. Herde, E. & Tan, J. (2009). A review of solid materials as an alter native ammonia sources for lean NOx reduction with SCR. Diesel Exhaust Emission Control, 2009-2011.

Gouveia, L. (2011). Microalgae as a feedstock for biofuels. New York: Springer. doi:978-3-642-17006-9.

Grady, C. P. et al. (1999). Biological Wastewater Treatment. New York: Marcel Dekker.

Huang, J.C., et al. (2013). Development of a constructed wet-land water treatment system for selenium removal: Incorporation of an algal treatment component. Environmental Science & Tech-nology.

Hunter-Cevera, J. (n.d.), Sustainable development cf algae biofuels. In: Sustainable development of algal biofuel.Pdf.

Jian, A., et al. (2011). Combined nutrient recovery and biogas scrubbing system integrated in series with anumal manure anaerobic digester.

Kaminsky, W. et al. (2011). Biobutanol-production and purifica-tion methods. Econogical Chemistry and Engineering, 18(1): 31-37.

Lee, J.W. (2013). Synthetic biology for photobiological produc-tion of butanoland related higher alcohols from carbon dioxide and water. In Advanced Biofuels and Bioproducts (pp. 441-521). New York: Springer. doi:10.1007/978-1-4614-4_22.

Lee, S.Y. et al. (2008). Fermentative butanol produciton by Clostridia. Biotechnology and Bioengineering, 101(2), 209-28. doi:10.1002/bit,22003.

Lin, S., et al. (2007). Water and Wastewater Calculations Manual. New York: McGraw-Hill.

Microalgae: Biotechnology and Microbiology. (1994). Microalgae New York: Cambridge University Press.

Millar, D.N. et al. (2013). Background information on the MSU-EPRI N20 offsets protocol. Background information MSU-EPRI N20 offset.Pdf [EPRI Report].

Ni, B., et al. (2001). Modeling nitrous oxide production during biological nitrogen removal via nitrification and deni trification. Extension of the ASM models. Environmental Science & Technology, 45(18): 7768-7776.

Pinder, R.W., et al. (2007). Ammonia emission controls as a cost-effective strategy for reducing atmospheric particulate matter in the easter United States. Environmental Science & Technology, 41(2): 380-386. doi:10.1021/es060379a.

Sab, E.P.A. (nd.). Reactive nitrogen in the United States: An analysis of inputs, flows, consequences and management options.

Spencer III, H.W., et al. (2007). Design considerations for generating ammonia from urea for NOx control with SCRS.

Kato, S., A.R.E. (1004). Report to the Legislature Gas-Fired Tower Plant NOx Emission Controls and Relatved Environmental Impacts. Gas-Fired,Power Plant NOx Emission Controls and Report.Pdf (CA Report to the Legislature).

Sutton, M.A. (2011). The European Nitrogen Assessment. Cambridge University Press.

Ward, B.., (2013). Oceans. How Nitrogen is Lost. Science 341 (6144(: 352-3. doi:10.1126/science.1240314.

Zheng, Y.N., et al. (2009). Problems with the microbial production of butanol. J. Industrial Microbiology & Biotech-nology, 36(9), 1127-38. doi:10.1007/s10295-009-0609-9.

* cited by examiner

Volatile Gas Stripping / Concentration

APPLICATIONS OF THE ROTATING PHOTOBIOREACTOR

CROSS REFERENCE TO RELATED APPLICATIONS

This is a divisional of U.S. patent application Ser. No. 13/987,795 filed on Sep. 3, 2013, now U.S. Pat. No. 8,895,279. This application claims the benefit of provisional Application No. 61/743,380 by the same applicant for the same invention, filed Sep. 4, 2012, and is a continuation-in-part of application Ser. No. 13/373,860, filed on Dec. 1, 2011. application Ser. No. 13/373,860 claims the benefit of provisional Application No. 61/460,219, filed Dec. 29, 2010. All of the above are incorporated herein expressly by reference in their entirety.

STATEMENT REGARDING GOVERNMENT RESEARCH

The U.S. Department of Agriculture funded proof of concept research under U.S. Department of Agriculture 2010 SBIR project number 2010-33610-20920.

BACKGROUND OF THE INVENTION

1. Field of Invention

This invention is a bioreactor that can support a large fixed microbial or autotrophic biofilm that consumes soluble organic or inorganic substrates while producing a nutrient rich biomass and gases such as hydrogen, oxygen, biofuels, and ammonia, that are harvested for a beneficial purpose. This invention can be applied to a variety of processes for recovering valuable gases, nutrients, and products produced from different substrates by autotrophic organisms in a single reactor without the use of chemicals and with minimal energy inputs. Applications include nutrient removal and harvesting from a variety of water bodies, volatile or semi-volatile gas stripping, concentration of stripped gases, and compost biogenic drying.

2. Background

Nutrients discharged from agricultural operations, waste management, and bioenergy processing facilities are significant environmental problems adversely affecting over 30% of our nations waters. The National Academy of Engineering of the National Academies recently published the "Grand Challenges for Engineering," posted at http://www.engineeringchallenges.org/_cms/challenges.aspx. One of the 14 challenges was "Manage the Nitrogen Cycle". The "nitrogen issue" is the result of twice as much nitrogen being introduced into the world through anthropogenic sources as introduced from natural sources. The ability to produce reactive nitrogen through the Haber-Bosch process has enabled man to feed the world. However, that engineering miracle has totally distorted the nitrogen cycle leading to significant environmental and public health problems. Seventy five percent of the additional anthropogenic reactive nitrogen input is converted to $N_2$ gas through denitrification, a process that converts a portion (2% to 6%) of the nitrogen to the powerful greenhouse gas $N_2O$, which has an atmospheric lifetime of over 100 years. Aside from being a powerful GHG at 310 times $CO_2$, $N_2O$ is now the primary cause of stratospheric ozone depletion. The remaining 25% of the added reactive nitrogen is accumulated in the soils, groundwater, rivers, estuaries, and oceans modifying those terrestrial and aquatic environments. The adverse impacts of nitrogen include the production of fine particulate matter that is responsible for atmospheric haze and increased human mortality, increased nitrate levels in groundwater, acidification of surface water, harmful toxin producing algae blooms, hypoxia in coastal waters, forestry decline, and loss of terrestrial biodiversity.

Solutions to the "nitrogen problem" have primarily been through the use of engineered denitrification systems that increase the NOx, $N_2O$, and fine particulate matter emissions to the atmosphere. Some processes attempt to recover and reuse ammonia and thereby reduce the industrial production of ammonia through the Haber-Bosch process. Ion exchange, membrane separation, and stripping technologies have all been used. The recovery processes invariably sequester the ammonia as dilute acidic solutions of ammonium sulfate or ammonium nitrate. Those processes have been shown to be uneconomical technologies.

Soluble phosphorus and nitrogen are the primary concern. Technology is required to economically remove soluble nitrogen, phosphorus, and potassium nutrients discharged from waste treatment, agricultural fields, or bioenergy facilities. Such facilities include manure management, food processing, wastewater treatment, and renewable energy production such as anaerobic digestion where a majority of the particulate organic nutrients are converted to soluble ammonia and phosphate.

A large variety of expensive technologies have been developed to remove both soluble nitrogen and phosphate from wastewater streams. Phosphate removal by chemical precipitation, biological assimilation, or crystallization (MAP, struvite) precipitation is expensive. Ammonia nitrogen removal by stripping, biological nitrification/denitrification, ammonia oxidation (Anammox) or precipitation as ammonium sulfate, nitrate, or phosphate is also expensive. Wetlands or constructed marshes are the least expensive but occupy large tracts of land where nutrient accumulation may not be sustainable.

Conversion of soluble nutrients to particulate matter, such as micro and macro algae is an attractive method for removing soluble nutrients. However, the limited productivity, ammonia toxicity, and cost of harvesting have prevented widespread adoption. Algae or cyanobacteria growth is limited by the turbidity that such growth imparts to the liquid. Light penetration is reduced in direct proportion to the algae biomass concentration. Pond surface area also limits $CO_2$ transfer to the growing algae thereby limiting productivity. Variable depth and energy consuming gas injection photobioreactors have been proposed to overcome such limitations.

Ammonia toxicity is also a significant problem requiring dilutions of up to 20 to 1 for anaerobic digestate. Ammonia concentrations exceeding 100 ppm are inhibitory to autotrophic growth. Nitrogen loss to the atmosphere is also a significant problem in high pH systems. The loss of nitrogen to the atmosphere led the National Academy of Science to conclude that the growth of algae for biofuel production was unsustainable. "The estimated requirement for nitrogen and phosphorus needed to produce algal biofuels necessary to meet 5% of US transportation fuel ranges from 6 million to 15 million metric tons of nitrogen and from 1 million to 2 million metric tons of phosphorus if the nutrients are not recycled or included and used in co-products. Those estimated requirements represent 44 to 107 percent of the total nitrogen use and 20 to 51 percent of total phosphorus use in the United States."

Finally, harvesting a highly concentrated biomass containing the recovered nutrients is expensive. The algae biomass separation and concentration is the most expensive unit process, representing 20 to 30% of the total cost of algae production and recovery systems. The limited productivity results in slow nutrient recovery in larger than desired reactors. Additional equipment for biomass nutrient separation and concentration increases the cost considerably.

The autotrophic rotating photobioreactor (RPB) is similar to the heterotrophic rotating biological contactor (RBC), a waste treatment device used to support large heterotrophic bacterial populations for the enhanced removal of soluble organic waste constituents flowing through the RBC. In fact, a rotating bioreactor contactor can be converted into a rotating photobioreactor by adding to it a light source directed at the microorganisms, using autotrophic micoorganisms, and providing a carbon source, such as carbon dioxide or bicarbonate. A variety of configurations and devices exist for heterotrophic waste treatment. The following U.S. patents are representative of the development of the art: U.S. Pat. No. 1,811,181 (an original disclosure of an open RBC, issued in 1931); U.S. Pat. No. 1,947,777 (an enclosed heat exchanger, adsorption unit, issued in 1934); U.S. Pat. No. 3,630,366 (the typical open conventional RBC, issued in 1971); U.S. Pat. No. 3,704,783 (an aerated fixed film RBC, issued in 1972); U.S. Pat. No. 3,904,525 (a pre-aerated spray RBC issued in 1975); U.S. Pat. No. 4,115,268 (an open or closed RBC with an alternative rotor design, issued in 1978); U.S. Pat. No. 4,137,172 (an attached growth RBC with corrugated disks, operating at 40% submergence, issued in 1979); U.S. Pat. No. 4,289,620 (a RBC in combination with an adsorbent, issued in 1981); U.S. Pat. No. 4,330,408 (a partially submerged RBC incorporating suffusing a portion of disc with air, issued in 1982); U.S. Pat. No. 4,345,997 (an RBC with unique disc ribs, issued in 1982); U.S. Pat. No. 4,385,987 (a RBC with alternative structural design of the discs, issued in 1983); U.S. Pat. No. 4,431,537 issued in 1984; U.S. Pat. No. 4,444,658 issued in 1984); U.S. Pat. No. 4,537,678 issued in 1985); U.S. Pat. No. 4,549,962 issued in 1985); U.S. Pat. No. 5,401,398 issued in 1995); U.S. Pat. No. 5,458,817, issued in 1995); U.S. Pat. No. 5,498,376 issued in 1996; U.S. Pat. No. 5,637,263 issued in 1997); U.S. Pat. No. 5,714,097 issued in 1998); U.S. Pat. No. 5,851,636 (ceramic plates) issued in 1998); U.S. Pat. No. 6,071,593 (grooved ceramic packing) issued in 2000); U.S. Pat. No. 6,241,222 issued in 2001); U.S. Pat. No. 6,783,669 issued in 2004); U.S. Pat. No. 7,156,986 issued in 2007); U.S. Pat. No. 8,460,548 issued in 2013); U.S. Pat. No. 4,563,282 (a RBC incorporating microscreens in conjunction with rotating biological contactors that are placed in a primary settling tank, the aeration tank and a final clarification tank, issued in 1986); U.S. Pat. No. 4,568,457 (an anaerobic RBC incorporating acid and methane phase segments, issued in 1986); U.S. Pat. No. 4,604,206 (a staged anaerobic digestion RBC, issued in 1986); U.S. Pat. No. 4,668,387 (an aerated, completely submerged air-driven RBC, issued in 1987); U.S. Pat. No. 4,692,250 (a recirculating staged waste water treatment RBC, issued in 1987); U.S. Pat. No. 4,721,570 (a RBC with a solids contact zone, issued in 1988); U.S. Pat. Nos. 4,729,828 and 4,737,278 (a modular rotating biological contactor apparatus, issued in 1988); U.S. Pat. No. 5,326,459 (a two-stage RBC with different diameter discs, issued in 1994); U.S. Pat. No. 5,395,528 (a complex sewage treatment apparatus incorporating a RBC, issued in 1995); U.S. Pat. No. 5,407,578 (a partitioned RBC capable of addressing toxic inputs, issued in 1995); U.S. Pat. No. 5,853,591 (a hydraulically driven RBC, issued in 1998); U.S. Pat. No. 6,403,366 (a rotating biofilter scrubber for removing air pollutants, issued in 2002); U.S. Pat. No. 7,083,720 (a modular expandable RBC, issued in 2006); U.S. Pat. No. 8,191,868 (a Rotating Inverse Biological Contactor (RIBC), issued in 2012); and U.S. Pat. No. 8,398,828 (an RBC incorporating photocatalytic degradation with UV light, issued in 2013). Relevant U.S. patent applications include: No. 20050133444 (self-cleansing media, filed in 2005); a patent application for a double-sided, self-cleaning media, filed in 2007; No. 20080053880 (configurable RBC application, filed in 2008); No. 20080210610 (RBC that could be inoculated with various bacteria, filed in 2008).

The patent history displays a wide variety of configurations and arrangements for the aerobic or anaerobic treatment of wastewater through the retained growth of a bacterial biofilm on the RBC rotating surface in open or enclosed reactors. A large heterotrophic, as opposed to autotrophic biomass population is achieved, but gases are not managed and stripping of end products has not been practiced.

Figure 2:
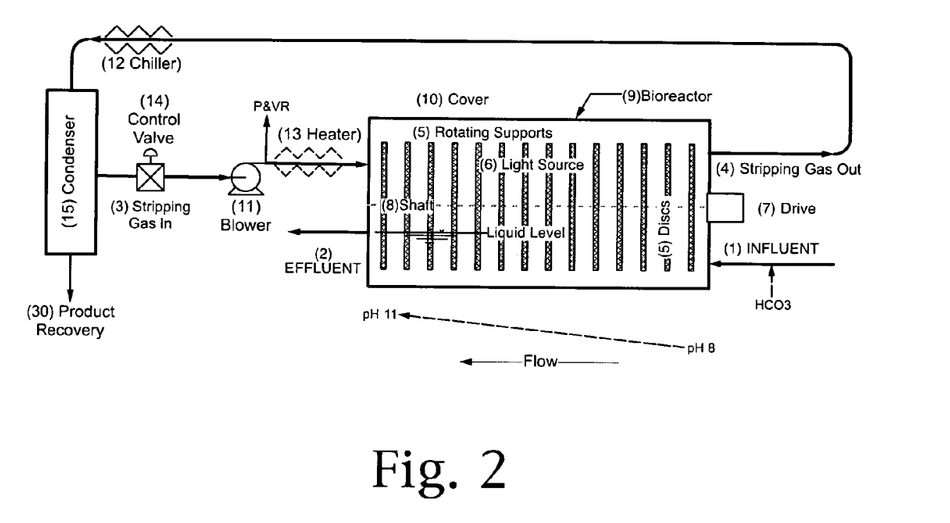
FIG. 2 is an elevational view of volatile gas stripping and recovery utilizing the rotating photobioreactor as a combined bioreactor and stripping unit.

U.S. patent application Ser. No. 13/373,860 of Burke, entitled Ammonia Nitrogen Recovery Through a Biological Process, filed on Dec. 1, 2011, disclosed use of a biofilm in a rotating photobioreactor (RBC) to support bicarbonate consumption through the growth of autotrophic organisms, thereby increasing the pH and shifting ammonium to ammonia gas for subsequent stripping. That application claimed a process whereby the pH was increased and the ammonia gas stripped in the same reactor without the use of chemicals, as shown in FIG. 2. Ammonia gas was produced and stripped, thereby reducing end-product inhibition while maintaining concentrated biomass for maximum ammonium to ammonia conversion. The configuration specified in U.S. patent application Ser. No. 13/373,860 has many other applications, some of which are the subject of the present invention. Important benefits of the process include the support of a large retained biomass population as a fixed film, removal of inhibitory end products while they are produced, ease of harvesting the biomass, and low energy inputs.

SUMMARY OF INVENTION

The rotating photobioreactor (RPB) was developed to overcome the nutrient removal limitations associated with conventional autotrophic organism growth in ponds or reactors. The rotating photobioreactor (RPB) is an improved method of producing biomass for energy production, as well as removing and concentrating nutrients from waste streams and/or eutrophic waters. The bioreactor is capable of providing high surface to volume ratios (S/V) for maximum light exposure, photo-autotrophic growth, gas transfer, and oxygen production. The RPB can be open or enclosed. It can be mounted in a vessel such as a tank or placed in a water body. "Vessel" is broadly defined to include, without limitation, a container, receptacle, repository such as a tank, water body, lake, river or stream, liquid conveyance or transport channel. The RPB enables efficient harvesting of concentrated nutrient laden biomass. Those attributes make the RPB an attractive, simple, economical, and scalable method for removing soluble nutrients (NPK) from waste streams. The process is a low head gas production and management apparatus that produces oxygen, while consuming $CO_2$. The RPB is a sustainable nutrient waste treatment technology that incorporates a method to economically concentrate and separate the nutrient laden, biomass for use as a fertilizer or renewable energy source.

The RPB was originally developed as a method to increase the pH of anaerobic digestate without the use of chemicals for the stripping and recovery of ammonia nitrogen (Burke, U.S. patent application Ser. No. 13/373,860, entitled Ammonia Nitrogen Recovery Through a Biological Process, filed Dec. 1, 2011). It was known that autotrophs consume bicarbonate and thereby increase the liquid pH when the amount of carbon dioxide present is low enough to be growth limiting. However, the use of algae or cyanobacteria presented a number of problems. Ammonia is toxic to autotrophs and significantly reduces their specific growth rate. Consequently, it was necessary to develop a large biomass for sufficient growth to occur and thereby consume the bicarbonate to provide an increased pH at low specific growth rates. The development of a large cyanobacterial mass required a large phototrophic surface to volume ratio (S/V). But developing a large surface to volume ratio was hindered by the color and turbidity of the digestate as well as turbidity produced through autotrophic growth. The color, turbidity, and autotrophic concentration reduced the photic zone in which autotroph growth occurs. All of those deficiencies can be overcome by using attached autotrophic growth apparatus, i.e., the RPB. Growth occurs on plates or rotating solid or semisolid surfaces constructed of a variety of materials upon which organisms attach and form a biofilm.

Figure 1:
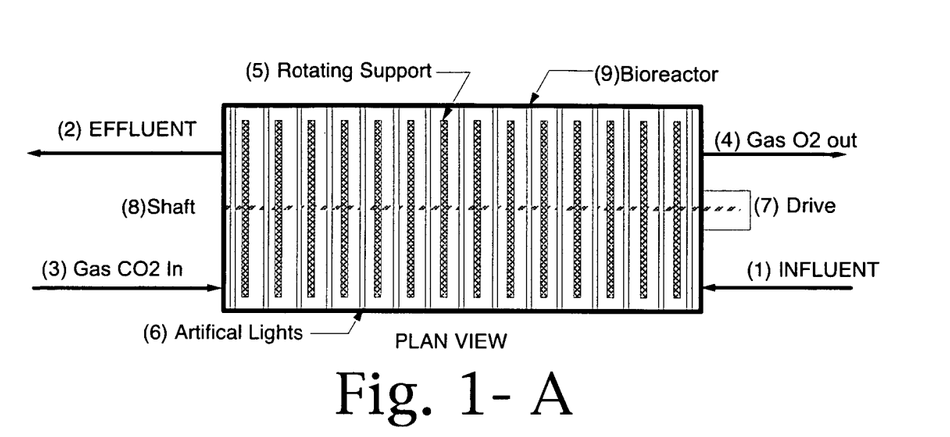

The process/apparatus, called an attached growth, rotating photobioreactor (RPB), uses natural or genetically-engineered organisms that attach to a rotating support media upon which autotrophic organisms grow. The media consists of a series of plates or plate-shaped media that maximize light exposure and gas exchange within an enclosed or open reactor. An example of the apparatus is as shown in FIG. 1. The attributes of the process are as follows:

A) Surface to Volume Ratio (S/V). The apparatus provides a very large surface to volume ratio for light exposure as well as gas transfer. The rotating photobioreactor is truly three dimensional since the biomass growth surface is proportional to twice (i.e., both sides) the square of the plate diameter. Providing a rough or contoured surface can increase that surface area. Turbid liquids can be processed since the liquid depth over the biomass growth surface is very low, permitting adequate light penetration. The diameter and distance between the plates controls the S/V ratio. In a square algae pond the total surface to volume ratio is equal to 1/d, where d=depth, whereas in the same area the RPB S/V is equal to approximately twice that of a pond (2/d) if d is approximately equal to the disc spacing and no surface area enhancements are included. That distance between the plates can be low if artificial light sources (e.g., light-emitting diodes) are placed between the plates.

B) Light Exposure—Light penetration is hindered in conventional photobioreactors since the photic zone, that is a function of turbidity, is commonly less than 4 inches. In the RPB, exposure to light is independent of liquid depth and turbidity. Light can be supplied by natural or artificial means. Light exposure is controlled by the surface area of the rotating growth plates, the radiant flux of light provided, and the speed of rotation. The rotation speed can be controlled to maximize light exposure, organism shading, and gas transfer. The rotation speed and enclosed reactor provide a means to control temperature and exposure to predation, thereby minimizing any adverse environmental effects. The artificial light source can be easily accessed for repair and maintenance since it can be located in the wall of the photobioreactor. Typically the lights are above or between the plates and above the water surface for ease of maintenance.

C) Water Losses—The loss of water vapor may also be minimized by condensing water vapor from the gases exiting the enclosed rotating photobioreactor.

D) Solids Retention Time—Most importantly, the reactor maximizes the solids retention time of the organisms that remove chemical constituents from the liquid or generate gases. The reactor can produce a non-turbid effluent since the growth occurs on the rotating plates. No matter the application, the RPB will produce energy-yielding biomass or gases from the supplied $CO_2$. The biomass can be recovered at a rate to maximize yield.

E) Biomass Harvesting. Harvesting algae or cyanobacteria is typically an expensive unit process representing 20 to 30% of the total cost of algae biomass production. Commonly used processes include centrifugation, flotation, flocculation with a variety of flocculants and sedimentation, membrane filtration, ultrasonic separation, froth flotation, and electrolysis. A variety of harvesting technologies have recently been developed. Relevant recent U.S. patents include U.S. Pat. No. 8,470,161 (electrolysis is used to separate lipids within the bioreactor); U.S. Pat. No. 8,399,239 (an attachment element such as iron oxide, steel, iron, silica, etc. is introduced to attach to the algae and thereby improve removal through settling or magnetic means); and U.S. Pat. No. 8,281,515 (algae are grown in aggregated clumps or on synthetic fabric that is removed and recovered from the growth medium).

In contrast, the RPB attached biomass can be easily harvested. The concentrated solids can be removed from the rotating plates through any of a variety of means such as periodic scraping or partial scraping with a blade to discharge the aggregated solids to the liquid media for removal through settling. Concentrated biomass is preferably removed from the rotating surface of the growth plates with a vacuum suction device that periodically removes a portion of the biomass from different sections of the rotating surface like a record player stylus. Concentrated biomass at 10% plus is accumulated in a vacuum receiver. That biomass can be delivered to an energy producing process to recover the energy value as an oil, sugar, or biomethane gas. The biomass may also be further dried to produce a fertilizer in a powder or pellet form.

F) Nutrient Harvesting. Autrotrophic organisms can harvest soluble nutrients in direct proportion to their growth rate. The growth rate is generally controlled by the limiting nutrient, light. The nutrients can subsequently be economically harvested with the biomass.

G) Gas Processing. It is necessary to supply $CO_2$ for autotrophic organism growth while removing the inhibiting $O_2$. Other gaseous products that can be produced by the process such as butanol or selenium can also be efficiently removed and subsequently condensed at low pressure as shown in FIG. 2. "Product" is broadly defined to include without limitation a recovered commodity produced from a substrate through a physical or biochemical process. The process provides the ability to remove and recover gaseous products at atmospheric pressure while providing essential gases such as carbon dioxide for organism growth with minimal energy input. It is a volatile gas transfer reactor.

"Volatile" is broadly defined to include, without limitation, an evaporative or vaporous substance such as water, alcohol, and gases such as ammonia ($NH_3$) that are evaporated at normal temperatures. Unlike conventional photobioreactors, the gas supply containing $CO_2$ is delivered at low atmospheric pressure. In other processes, such as butanol production, the toxic end product, butanol can be easily removed by blowing gas across the surface of the plates as shown in FIG. 2, as opposed to energy-consuming gas stripping through foam-producing bubble aeration.

Figure 3:
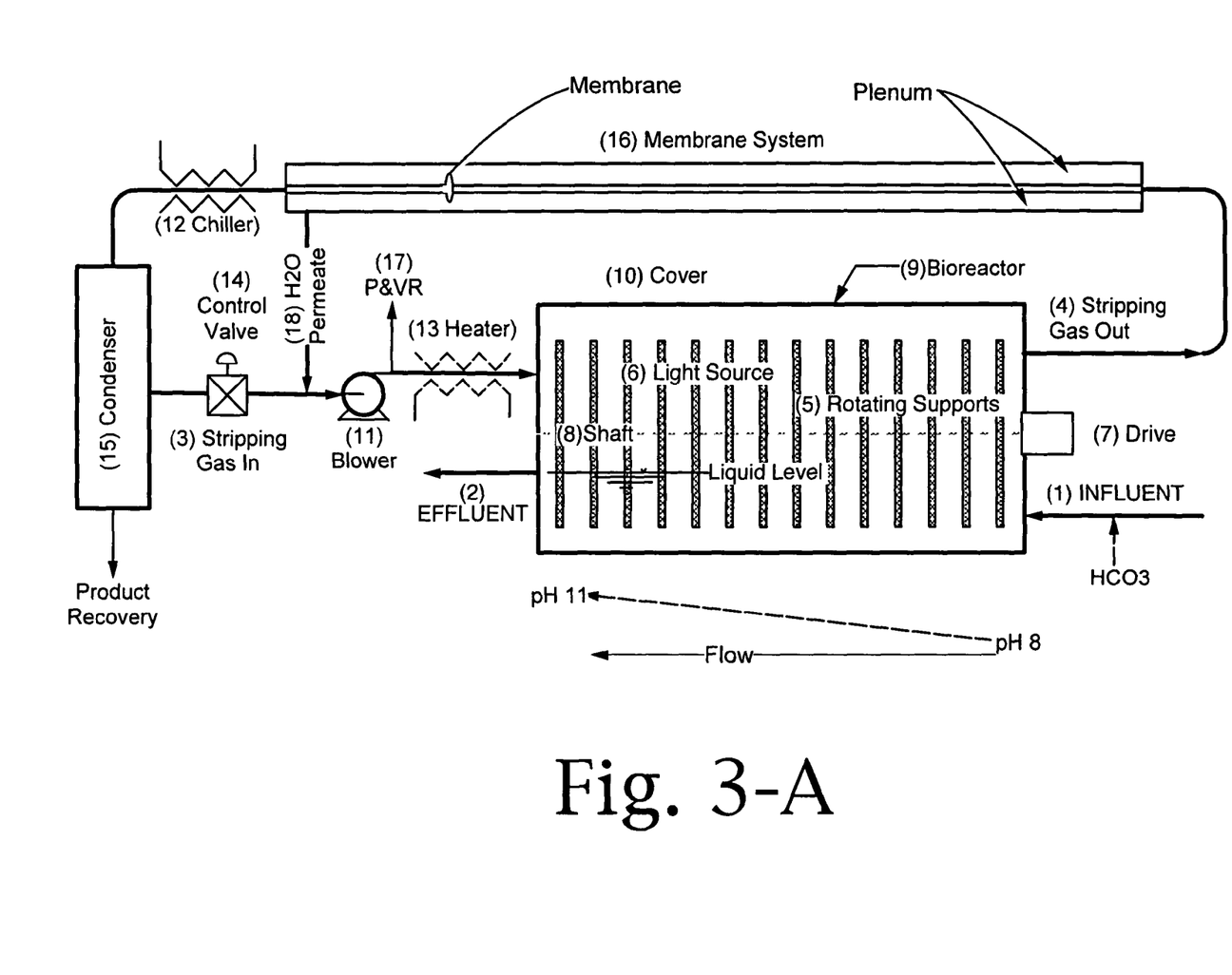

H) Product Gas Concentration. The volatile product gases that are stripped include water vapor, which dilutes the final, condensed product unless steps are taken to overcome the dilution. The RPB can incorporate a membrane concentration device that passes permeate water vapor and latent heat back to the reactor thus producing a higher concentration retentate product as shown in FIG. 3. In most cases the higher concentration product has significantly greater commercial value. For example higher concentration ammonia solutions have value for the pretreatment of lignocellulosic biomass for the production of energy. In another application the RPB concentration process can be adapted to produce diesel exhaust fluid having a concentration of 20% ammonia thereby reducing the discharge of NOx to the environment. Diesel exhaust fluids are typically composed of a 33% solution of urea in distilled water, thereby producing a 20% reactive ammonia solution.

I) Energy Inputs—The RPB energy inputs for liquid and $CO_2$ gas supply are extremely low because it is a free-flowing, low gas pressure, low liquid head process. Oxygen is removed at atmospheric pressure. Unlike conventional photobioreactors, the gas supply containing $CO_2$ is continuously delivered at low atmospheric pressure. Gas transfer, $CO_2$ in/$O_2$ out, as well as product gas removal are rapid and unrestricted for the same reasons. Heat can be provided as needed to maintain optimum operating conditions.

J) pH control—The process can also control the pH of the liquid through cyanobacterial consumption of bicarbonate. An optimal pH of 8.3 can be maintained or the pH may be increased to control predation by other organisms or for stripping gases by simply adjusting $CO_2$ inputs in the form of a gas or as bicarbonate. The unhindered light exposure and ability to control the pH will provide a degree of disinfection and predation control.

Figure 4:
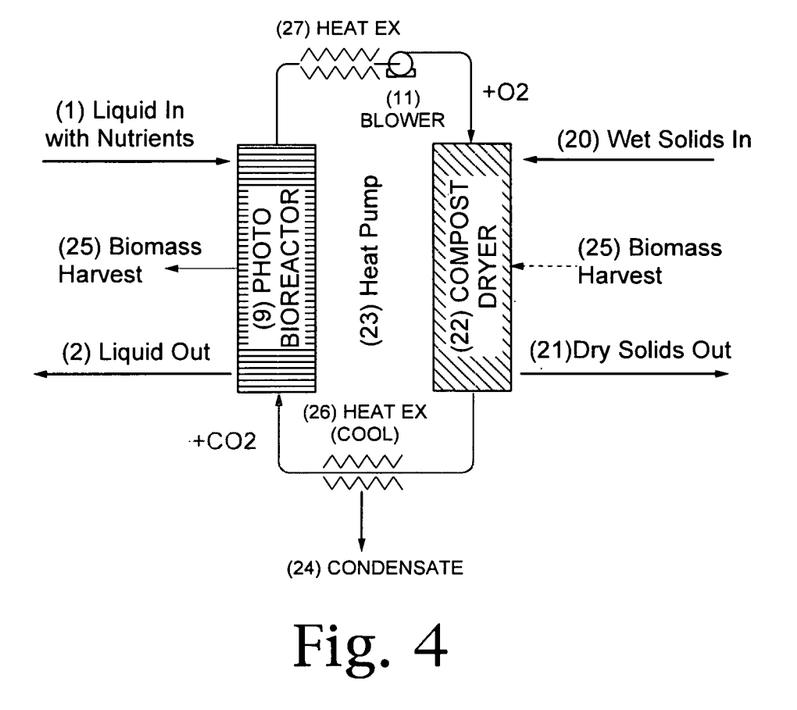
FIG. 4 presents the rotating photobioreactor integrated with a composting/drying reactor process.
Figure 5:
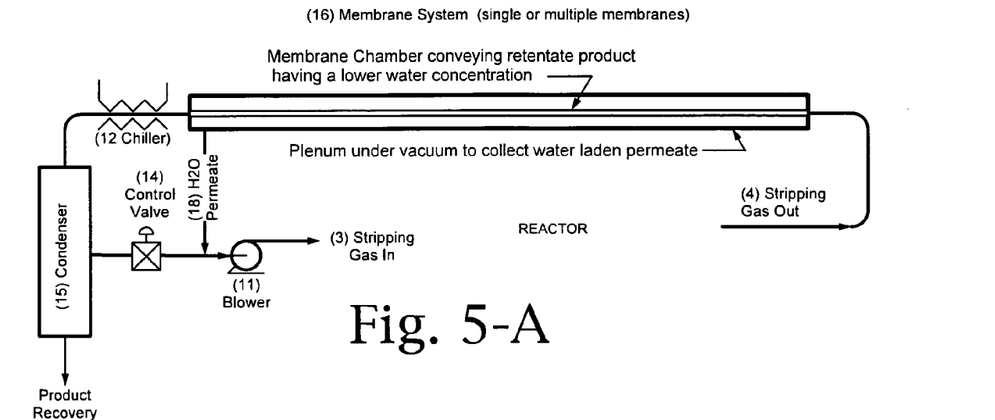

K) Process Integration—The process produces large quantities of oxygen that can be used for a variety of purposes. The effluent liquid is fully saturated and can be supersaturated with oxygen. The growth of autotrophic organisms will convert soluble nutrients to solid biomass for removal. The oxygen generated can be used for a variety of purposes such as wastewater treatment or stabilization and biogenic drying of processed biomass solids. Ideally an RPB would be placed between primary treatment units and aerated waste activated sludge treatment units at a wastewater treatment plant to remove and reclaim nutrients and oxygenate the influent to the secondary aeration tanks. The process can also be integrated with solids composting. Anaerobic digestate solids are commonly stabilized by composting the residual solids. The compost/drying process can be integrated with the RPB process that produces oxygen for composting while the composting process produces the $CO_2$ for the RPB process as shown in FIG. 4. Such an arrangement reduces the discharge of gases, including odorous compounds to the environment.

L) Ammonia Stripping—Initially the process was developed to raise the pH of anaerobic digestate, pass the high pH liquid through a stripping tower, and then strip and recover the ammonia. However, during the initial operation it was discovered that ammonia gas was evolved as the liquid passed through the RPB and the pH increased from an initial value of 8.3 to 10. The rapid emission of ammonia gas, as the pH increased, created biomass toxicity since it was the unionized ammonia that inhibited the cyanobacteria. A fan was placed in the photobioreactor to remove gaseous ammonia. It became apparent that the RPB could be used for both raising the pH and stripping the ammonia in a common unit, as shown in FIG. 2, at significantly less cost and power consumption than a conventional stripping tower.

M) Managing End Product Toxicity—Removal of end products that inhibit production of desired products is the goal of most fermentation processes. Typically the processes to improve recovery performance and reduce costs include adsorption, pervaporation, liquid-liquid extraction, gas stripping, and reverse osmosis. Reverse osmosis has the disadvantage of membrane clogging or fouling. In contrast, liquid-liquid extraction has high capacity and selectivity, although it can be expensive to perform. Gas stripping by bubbling fine or coarse bubbles through the fermentation broth is a simple but efficient way to recover volatile products from fermentation. Gas stripping enables the use of a concentrated solution in the fermentor and a reduction in end product inhibition. However, gas stripping requires compressor and turbine energy. Foaming has been a problem requiring toxic foam suppression chemicals. Liquid-liquid extraction is another efficient technique to remove solvents from the fermentation broth. Liquid-liquid extraction has critical problems such as the toxicity of the extractant to the microbial cell and emulsion formation. Pervaporation is a membrane-based process that allows selective removal of volatile compounds from the fermentation broth. Further distillation is required. The rotating bioreactor facilitates a stripping process that operates at low pressures by blowing gas across the attached biofilm growth surface, as shown in FIGS. 2, 3-A and 3-B.

Foam is not produced with such an arrangement. The disclosed process of stripping in attached growth bioreactors can be applied to heterotrophic (FIG. 3-B) as well as autotrophic (FIG. 3-A) reactors.

BRIEF DESCRIPTION OF DRAWINGS

FIG. 1-A presents a general plan of a covered or uncovered rotating photobioreactor; and FIG. 1-B is an elevational view thereof.

FIG. 3-A presents volatile gas stripping and concentration utilizing the rotating photobioreactor as a combined bioreactor, stripping, concentration and recovery unit.

FIG. 3-B presents volatile gas stripping and concentration utilizing the rotating biological contactor as a combined bioreactor, stripping, concentration and recovery unit.

FIG. 5-A presents an example of the membrane water vapor separation system; and

FIG. 5-B presents a cross-sectional view thereof.

DETAILED DESCRIPTION OF INVENTION

The rotating photobioreactor (RPB) is a fixed film reactor upon which autotrophic organisms are grown as a biofilm. A basic schematic of the reactor is shown in FIGS. 1-A and 1-B. It consists of a series of solid or semi-solid rotating plates or discs (5) that support the growth of a biofilm. The photobioreactor can be open or closed, covered (10) or uncovered. It can be mounted in a vessel such as a reactor tank (9), stream channel or water body, waste conveyance channel, etc. The reactor can use natural or artificial light (6). Lighting can be above (6), between (11), or below the rotating discs. The discs are supported on a shaft (8) and driven by any of a variety of drives (7) that can impart a rotating movement to the media.

The media upon which the autotrophic organisms are grown may consist of a variety of substances such as wood, cloth, porous ceramics, glass fiber, carbon fiber, etc. Modifying the topography or roughness of the surface can increase the plate area. The RPB may incorporate a variety of biomass harvesting devices (20) such as doctor blades that remove excess biomass growth and discharge the mass to the liquid stream for downstream removal. Vacuum suction devices may remove excess growth from any portion of the rotating discs and discharge the concentrated solids to a vacuum receiver.

Operation of the rotating photobioreactor requires an influent stream (1) containing essential nutrients, light (6), and a carbon source such as air with carbon dioxide (3), carbon dioxide, or bicarbonate. While recovering nutrients, the reactors produce an effluent gas (4) containing oxygen. The reactor may operate at thermophilic, mesophilic, or psychrophilic temperatures depending on the requirements for the growth of organisms retained on the rotating media.

Growth of the autotrophic organisms removes a portion of the soluble essential nutrients from the influent stream and carbon dioxide from the gas stream to produce particulate biomass that can be harvested (25), thereby removing the essential nutrients from the liquid stream and producing an effluent (2) deficient in nutrients. The rotating photobioreactor may also be used to harvest a variety of gaseous chemicals, such as ammonia, directly or indirectly produced by the autotrophic organisms. The RPB is a unique reactor in that the organisms are exposed to a liquid stream for a portion of the time and a gaseous stream for the remainder of the time. The fraction of the time exposed to either the liquid or the gaseous medium is controlled by the disk submergence or liquid level within the reactor. Products within the influent, or produced in the liquid medium, are carried to the gaseous portion of the reactor and thereby stripped with a circulating gas stream (3).

FIG. 2 presents an illustration of the stripping and recovery process. An influent stream (1) such as anaerobic digestate containing dissolved bicarbonate and dissolved ammonium enters an enclosed (10) rotating photobioreactor (9) having any of a variety of light sources (6) at a lower pH. As a liquid flows through the RPB the autotrophic organisms consume the bicarbonate causing the pH to increase from the influent value to values necessary to causes the ammonium to shift to ammonia gas that can be stripped by a gas flowing over the surface of the rotating plates. Supplemental bicarbonate ($HCO_3$) or carbon dioxide may be added to the influent streams to control growth.

The liquid influent may enter at any of a variety of ports along the lower portion of the reactor. The influent may also contain recirculated effluent to dilute the influent concentration and bicarbonate as required to maintain autotroph growth. The stripping gas (3), deficient in the product to be stripped, enters the upper portion, or gaseous portion, of the RPB at any of a variety of ports along the RPB necessary to achieve optimum gas flow over each plate surface. The stripping gas may exit (4) the RPB at any of a variety of outlet ports along the RPB necessary to achieve optimum product stripping and gas conveyance over each plate surface.

The stripping gas (4) containing the stripped product is conveyed to a condenser (15) cooled by a chiller (12) operating at a temperature less than the photobioreactor wherein the stripped water vapor and product (4) are condensed to form a condensate product (21) to be used for any beneficial purpose. The condenser produces an influent gas (3) deficient in the product that is then conveyed by a blower through a heater, if necessary, to the RPB to provide further stripping. Depending on the application the blower may provide sufficient heat. Excess stripping gas can be discharged and make up gas provided by a pressure and vacuum relief valve (P&VR) (17).

The process of stripping any gas from a liquid stream also removes water vapor that, when condensed, reduces the concentration of the product in the liquid stream since both liquid water and product are produced in the condenser. The concentration of the condensate is directly proportional to the product/water ratio of the stripped gas. As a result most stripping processes produce dilute solutions that have reduced value. In addition to producing a dilute solution the water vapor removes substantial quantities of heat from the reactor. This is a problem inherent in most stripping reactors. Minimizing the gas flow rate, stripping temperature, and condensing at higher temperatures will minimize dilution of the condensate product. Further concentration can be achieved through the use of a gas permeable membrane or membranes (16). The concentration process consists of utilizing a high water vapor permeable membrane such as a silicon gas permeable membrane SSP-M823, available from Specialty Silicone Products, Inc., Ballston Spa, New York, which has a high permeability rate for water vapor (3,500+) and lower permeability rates for ammonia (500), and stripping gases such as methane (80), nitrogen (25), and oxygen (50). The membrane is placed between the stripped gas stream and a plenum. A differential pressure is applied between the stripping gas stream consisting of the stripping gas, water vapor, and ammonia gas (retentate) and the lower pressure plenum gas stream (18)(permeate) composed of water vapor with lower concentrations of the stripping gas and ammonia. After passing through the membrane the stripping gas is depleted of water vapor while the plenum gas (18) is enriched. The plenum gas is then combined with the influent stripping gas from the condensate unit, thereby enriching the stripping gas with heat, water vapor, and minor concentrations of the product such as ammonia without significant loss of latent heat as shown in FIGS. 3-A and 3-B.

As shown in FIGS. 3-A and 3-B, one or more water vapor permeable membranes are installed on the stripping gas stream leaving the reactor, but prior to the chiller/condenser (15). The water permeable membranes are placed under a vacuum by the recirculating blower (11) and control valve (14), or another pressurization device, to cause the return flow of water vapor permeate with its latent heat to the photobioreactor.

The above-described product concentration process can be applied to a variety of stripping processes using a variety of substrates. "Substrate" is broadly defined to include, without limitation, a liquid stream or waste substance containing Nitrogen, Phosphorus, Potassium and other essential nutrients, including light required for autotrophic or heterotrophic organism growth, including organic compounds derived from the pretreatment or hydrolysis of cellulosic or lignocellulosic biomass selected from the group consisting of waste materials corn cobs, crop residues, corn husks, corn stover, grasses, wheat straw, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, human waste, sugar, algae, cyanobacteria and mixtures thereof. A highly concentrated aqua ammonia stream has significantly greater value if used in ammonia-soaking pretreatment of lignocellulosic biomass for renewable energy production (12+%) as well as in the production of diesel exhaust fluids (20+%). The membrane system presented here can produce both products.

The product recovery process (FIG. 2) and the product concentration process (FIG. 3-B) described above may also be applied to heterotrophic bioreactors such as the RBC to strip and recover "end products" such as butanol and other alcohols from fermentation processes without producing foam or utilizing excess energy. The RPB may also be integrated with composting or compost drying without producing odors inherent in those processes. Such a low pressure integration is shown in FIG. 4. The photobioreactor (9) is coupled with a solids compost or compost drying reactor (22). The photobioreactor receives a liquid or solid stream containing sufficient nutrients for autotrophic growth and produces a liquid stream deficient in nutrients. The photobioreactor also produces a biomass stream that can be harvested (25) for production of an organic fertilizer, input to the compost dryer, or converted to energy through any of a variety of thermochemical or biological processes such as anaerobic digestion. The photobioreactor also produces oxygen that can be stripped and transported through a suction or discharge blower (11) with or without a gas heat exchanger (27) to the enclosed biogenic compost dryer (22). Wet solids (20) are also input into the compost dryer with or without photobioreactor harvested biomass. The highly oxygenated organic biomass reacts in the reactor (22) producing carbon dioxide, heat, and water vapor. The reduced and biogenically dried organic compost is discharged from the reactor (22). The carbon dioxide enriched circulating gas stream containing heat and water vapor exits the compost reactor. The carbon dioxide gas stream may be cooled (26) and the condensate (24) recovered, a portion of which may be used in the photobioreactor. Cooling for condensate recovery (26) and heating (27) for the compost/dryer may be provided by a heat pump (23). The $CO_2$ produced in the compost/dryer (22) is then used in the photobioreactor to produce biomass and oxygen in the photobioreactor in a closed loop system. The process provides a means of compost drying without discharging odorous gases to the environment.

REFERENCES

Casey, T. J. (1997). *Unit treatment processes in water and wastewater engineering*. Chichester; New York: Wiley.

Corbitt, R. A. (1990). *Standard handbook of environmental engineering*. New York: McGraw-Hill.

Demirbas, A., & Demirbas, M. F. (2010). *Algae energy: Algae as a new source of biodiesel*. Springer.

*Design of Municipal Wastewater Treatment Plants*. (1992). Design of municipal wastewater treatment plants. Alexandria, Va.: Water Environment Federation; New York, N.Y.: American Society of Civil Engineers. Droste, R. L. (1997).

Eddy, M. &., Tchobanoglous, G., Burton, F. L., & Stensel, H. D. *Theory and practice of water and wastewater treatment*. New York: J. Wiley. (2003).

Ezeji, T. C., Karcher, P. M., Qureshi, N., & Blaschek, H. P. (2005). Improving performance of a gas stripping-based recovery system to remove butanol from *Clostridium beijerinckii* fermentation. *Bioprocess and Biosystems Engineering*, 27(3), 207-14. doi:10.1007/s00449-005-0403-7

Fulks, G., Fisher, G. B., Rahmoeller, K., Wu, M.-C., D Herde, E., & Tan, J. (2009). A review of solid materials as alternative ammonia sources for lean nox reduction with SCR. *Diesel Exhaust Emission Control*, 2009-2001.

Gouveia, L. (2011). *Microalgae as a feedstock for biofuels*. Heidelberg; New York: Springer. doi:978-3-642-17996-9

Grady, C. P. L., Daigger, G. T., & Lim, H. C. (1999). *Biological wastewater treatment*. New York: Marcel Dekker.

Huang, J. C., Suárez, M. C., Yang, S. I., Lin, Z., & Terry, N. (2013). Development of a constructed wetland water treatment system for selenium removal: Incorporation of an algal treatment component. *Environmental Science & Technology*.

Hunter-Cevera, J. (n.d.). Sustainable development of algae biofuels. In *Sustainable development of algal biofuel.Pdf*.

Jiang, A., Zhang, T., Frear, C., & Chen, S. (2011). Combined nutrient recovery and biogas scrubbing system integrated in series with animal manure anaerobic digester.

Kaminsky, W., Tomczak, E., & Gorak, A. (2011). Biobutanol-Production and purification methods. *ECOLOGICAL CHEMISTRY AND ENGINEERING*, 18(1), 31-37.

Lee, J. W. (2013). Synthetic biology for photobiological production of butanol and related higher alcohols from carbon dioxide and water. In *Advanced Biofuels and Bioproducts* (pp. 447-521). New York, N.Y.: Springer New York. doi:10.1007/978-1-4614-3348-4_22

Lee, S. Y., Park, J. H., Jang, S. H., Nielsen, L. K., Kim, J., & Jung, K. S. (2008). Fermentative butanol production by clostridia. *Biotechnology and Bioengineering*, 101(2), 209-28. doi:10.1002/bit.22003

Lin, S., & Lee, C. C. (2007). *Water and Wastewater Calculations Manual*. New York: McGraw-Hill.

Microalgae: *Biotechnology and Microbiology*. (1994). *Microalgae: Biotechnology and microbiology*. Cambridge; New York: Cambridge University Press.

Millar, D. N., & Adam, D. D. (2013). Background information on the MSU-EPRI N2O offsets protocol. *Background information MSU-EPRI N2O offset*.Pdf [EPRI Report] (EPRI Report).

Ni, B.-J., Ruscalleda, M. L., Pellicer-Nacher, C., & Smets, B. F. (2011). Modeling nitrous oxide production during biological nitrogen removal via nitrification and denitrification: Extensions to the general ASM models. *Environmental Science & Technology*, 45(18), 7768-7776.

Pinder, R. W., Adams, P. J., & Pandis, S. N. (2007). Ammonia emission controls as a cost-effective strategy for reducing atmospheric particulate matter in the eastern united states. *Environmental Science &Technology*, 41(2), 380-386. doi:10.1021/es060379a SAB, E. P. A. (n.d.). *Reactive nitrogen in the united states: An analysis of inputs, flows, consequences, and management options*.

Spencer III, H. W., Peters, H. J., & Hankins, W. (2007). Design considerations for generating ammonia from urea for NOx control with SCRS.

Stephanie Kato, A. R. E. (2004). Report To The Legislature Gas-Fired Power Plant NOx Emission Controls And Related Environmental Impacts. *Gas-Fired Power Plant NOx Emission Controls And Re.Pdf* (CA Report To The Legislature).

Sutton, M. A. (2011). *The European Nitrogen Assessment*. Cambridge University Press.

Ward, B. B. (2013). Oceans. How nitrogen is lost. *Science (New York, N.Y.)*, 341(6144), 352-3. doi:10.1126/science.1240314

Zheng, Y. N., Li, L. Z., Xian, M., Ma, Y. J., Yang, J. M., Xu, X., & He, D. Z. (2009). Problems with the microbial production of butanol. *Journal of Industrial Microbiology & Biotechnology*, 36(9), 1127-38. doi:10.1007/s10295-009-0609-9

I claim:

1. A process for recovering volatile and non-volatile products from a substrate-laden influent stream using microorganisms growing in a rotating bioreactor contactor, said bioreactor including a vessel, a shaft mounted for rotation within said vessel about a shaft axis, a plurality of axially spaced-apart, growth plates attached to the shaft, each of the plates having surfaces to which a fixed film of the microorganisms are attached, and means for rotating the shaft and plates about the axis, comprising the simultaneous steps of:
  (a) operating the rotating bioreactor as an aerobic, facultative or anaerobic reactor;
  (b) feeding the influent stream past the growth plates such that the growth plates are partially submerged within the stream, whereby, as they grow, the microorganisms convert the substrate to volatile products and accumulate biomass; and
  (c) passing a stripping gas past the growth plates to harvest the volatile products as stripped gas.

2. The process of claim 1, wherein the microorganisms include heterotrophic microorganisms capable of converting the substrate into alcohols whereby the stripped gas includes butanol or other linear or branched chain alcohols.

3. The process of claim 2, wherein the microorganisms include *Clostridium acetobutylicum*.

4. The process according to claim 2, further comprising inserting the stripped gas into a condenser cooled by a chiller and operating at a temperature less than the temperature of the liquid in the vessel, whereby the stripped gas and water vapor are condensed to form a condensate product and a gas that is deficient in said product.

5. The process of claim 4, further comprising recirculating the gas that is deficient in said product past the growth plates for further stripping.

6. The process of claim 5, wherein if the temperature of the gas that is deficient in said product is less than the temperature of the liquid in the vessel, further comprising heating said gas up to said temperature and recirculating said heated gas past the growth plates for further stripping.

7. The process of claim 5, further comprising discharging excess stripping gas and/or providing make up stripping gas through a pressure and vacuum relief valve.

8. The process according to claim 5, wherein the stripping gas includes one or more of air, methane, nitrogen and/or oxygen, comprising further concentrating the product by the steps of:
  (a) conveying the stripped gas to an upstream side of a membrane disposed within a plenum, said membrane having a high permeability rate for water and a lower permeability rate for the stripping gas, and said stripping gas stream comprising stripping gas, water vapor, and stripped gas;
  (b) applying a differential pressure between the upstream side of the membrane and an opposite downstream side of the membrane, whereby water vapor passes through the membrane to the downstream side of the membrane as water vapor permeate, and the gas on the upstream side of the membrane becomes depleted of water vapor as retentate gas; and
  (c) combining the water vapor permeate formed in step (b) with the retentate gas that is deficient in condensate product to form a combined stripping gas.

9. The method of claim 1, wherein a gas is introduced into the rotating bioreactor contactor above the influent stream to increase the growth rate of said microorganisms.

10. The method of claim 9, wherein the rotating bioreactor contact has been converted into a rotating photobioreactor by equipping the rotating bioreactor contactor with a light source directed at the microorganisms, said microorganisms include autotrophic microorganisms, and said introduced gas comprises carbon dioxide.

11. The method of claim 9, wherein said microorganisms include heterotrophic microorganisms and said introduced gas comprises oxygen.

12. A process for concentrating the chemical constituents of a stripping gas stream, regardless of the source of the stripping gas stream, using a membrane disposed within a plenum, said membrane having an upstream side and an opposite downstream side, said stream including stripping gases, water vapor, and stripped product gas, wherein said stripped product gas includes ammonia and/or volatile biomass fermentation products including butanol and other alcohols, comprising the steps of:
  (a) conveying the stripping gas stream to the upstream side of the membrane, said membrane having a high permeability rate for water and a lower permeability rate for the stripping gas;
  (b) applying a differential pressure between the upstream side of the membrane and the downstream side of the membrane, whereby water vapor passes through the membrane to the downstream side of the membrane as water vapor permeate, and the gas on the upstream side of the membrane becomes depleted of water vapor as retentate gas;
  (c) condensing the retentate gas formed in step (b) in a condenser to form condensate product and retentate gas that is deficient in said condensate product; and
  (d) combining the water vapor permeate formed in step (b) with the retentate gas that is deficient in condensate product to form a combined stripping gas.

13. The process of claim 12, further comprising passing the combined stripping gas past the growth plates of a rotating photobioreactor, said rotating photobioreactor including a vessel, a shaft mounted for rotation within said vessel about a shaft axis, a plurality of axially spaced-apart, growth plates attached to the shaft, each of the plates having surfaces to which a fixed film of the microorganisms are attached, means for rotating the shaft and plates about the axis at a user-selectable rotational speed, and illumination means, while simultaneously performing the steps of:
  (a) shining light upon the microorganisms with the illumination means;
  (b) optionally feeding a carbon source into the vessel; and
  (c) feeding the influent stream past the growth plates such that the growth plates are partially submerged within the stream, whereby, as they grow, the microorganisms remove nutrients from the influent stream, capture the nutrients in biomass, emit oxygen gas, and convert the influent stream to a nutrient-deficient effluent stream; and further comprising
  (d) using the harvesting means to remove a portion of the microorganisms from the surfaces of the growth plates.

14. The process of claim 13, further comprising passing the combined stripping gas through a heater to raise the temperature thereof up to the temperature of the liquid in the vessel, and then passing the heated, combined stripping gas past the growth plates.

15. The process according to claim 13, wherein the differential pressure across the membrane is maintained by a recirculating blower and control valve to cause the return flow of water vapor permeate with its latent heat to the rotating photobioreactor.

16. The process according to claim 12 or 13 wherein the condensate product comprises aqua ammonia concentrated to 10 percent (w/w) or more, suitable for use in the pretreatment of lignocellulosic biomass for renewable energy production.

17. The process according to claim 12, 13 or 14, wherein the condensate product comprises a highly concentrated aqua ammonia concentrated to 20 percent (w/w) or more, suitable for use as diesel exhaust fluid.

18. The process of claim 14, wherein the differential pressure across the membrane is maintained by a recirculating blower and control valve to cause the return flow of water vapor permeate with its latent heat to the rotating photobioreactor.

* * * * *